United States Patent [19]
Jefferson et al.

[11] Patent Number: 5,380,660
[45] Date of Patent: Jan. 10, 1995

[54] METHOD OF TREATING SERUM OR SERUM-CONTAINING MEDIUM TO INACTIVATE AN INHIBITOR OF HEPATOCYTE DIFFERENTIATION

[75] Inventors: Douglas M. Jefferson, Watertown; David E. Johnston, Natick, both of Mass.

[73] Assignee: New England Medical Center Hospitals, Inc., Boston, Mass.

[21] Appl. No.: 956,595

[22] Filed: Oct. 5, 1992

Related U.S. Application Data

[63] Continuation of Ser. No. 360,428, Jun. 2, 1989, abandoned, which is a continuation-in-part of Ser. No. 305,750, Feb. 2, 1989, abandoned.

[51] Int. Cl.[6] .............................................. C12N 5/00
[52] U.S. Cl. ............................ 435/240.3; 435/240.31; 435/240.2
[58] Field of Search ............. 435/240.2, 240.3, 240.31, 435/1, 2

[56] References Cited

U.S. PATENT DOCUMENTS

| | | | |
|---|---|---|---|
| 4,189,535 | 2/1980 | Dinka | 435/2 |
| 4,654,304 | 3/1987 | Seijiro et al. | 435/240 |
| 4,803,163 | 2/1989 | Fahey et al. | 435/240.2 |

FOREIGN PATENT DOCUMENTS

8402916  8/1984  WIPO ................. 435/240.3

OTHER PUBLICATIONS

Novros, et al., Improved Method for Accurate Quantitation of Total and Conjugated Bilirubin in Serum (Abstract) Biological Abstracts, vol. 69, No. 9, Abstract 55354, p. 5923 1979.
Lin, et al. Induction of Glucagon Sensitivity in a Transformed Kidney Cell Line by Prostaglandin $E_2$ and its Inhibition by Epidermal . . . Molecular and Cellular Biology, vol. 7, pp. 4324–4328 Dec. 1987.
Honma et al. (1982) Gann 73:97.
Gibson et al. (1984) J. Cell. Physiol. 119:119.
Parker et al. (1981) Leuk. Res. 5:123.
Paine et al. (1982) Biochem. Pharmacol. 31:1175.
Conti and Tesat (1986) J. Steroid Biochem. 24:749.
Lin et al. (1987) Mol. Cell. Biol. 7:4324.
Rathblat et al. (1976) In Vitro 12:554.
Chen (1967) J. Biol. Chem. 242:173.
Gianazza and Arnaud (1982) Biochem. J. 201:129.
Gianazza and Arnaud (1982) Biochem. J. 203:637.
Minuth (1983) Laboratory Investigation, 48:543.
Finbach et al. (1985) J. Cell. Physio. 123:228.
Boyum et al. (1987) Experimental Hematology. 15:508.
Evinger-Hodges et al. (1982) J. Cell. Biol. 93:395.
Clark, et al. "Experimental Biochemistry" Second Edition pp. 72–73.

*Primary Examiner*—Douglas W. Robinson
*Assistant Examiner*—Susan M. Dadio
*Attorney, Agent, or Firm*—Fish & Richardson

[57] ABSTRACT

A method of reducing the loss of differentiative functions of cells cultured in culture medium containing serum which includes an inhibitor of cellular differentiation. The method includes treating the serum or serum-containing medium to remove or inactivate the inhibitor.

7 Claims, 5 Drawing Sheets

METHOD OF TREATING SERUM OR SERUM-CONTAINING MEDIUM TO INACTIVATE AN INHIBITOR OF HEPATOCYTE DIFFERENTIATION

This invention was made in the course of work performed under grants or awards from the National Institutes of Health. The U.S. government has rights in the invention.

This application is a continuation of U.S. Ser. No. 07/360,428, filed Jun. 2, 1989, now abandoned, which is a continuation-in-part of U.S. Ser. No. 305,750 filed Feb. 2, 1989 now abandoned. The invention relates to the use of serum in cell culture.

BACKGROUND OF THE INVENTION

Growth of cells in medium containing serum has been the standard for cell culture for decades. Serum enhances cell adhesion to culture vessels, adhesiveness being a requirement for cell viability in vitro, and provides factors that promote cell growth and function.

Cells are capable of differentiating in vitro in response to specific signals, but the presence of serum in the culture medium often results in loss of differentiative functions, i.e., specific characteristics not found in the immature cell. For example, human myeloid leukemia cells were induced to differentiate by exposure to exogenous serine proteases or to 12-O-tetradecanoyl-phorbol-13-acetate (Honma et al., 1982, Gann 73: 97), and murine neuroblastoma cells were induced to differentiate in the presence of cAMP effectors (Gibson et al., 1984, J. Cell. Physiol. 119: 119), yet the level of morphological differentiation of these cells in medium containing fetal calf serum or calf serum was found to be significantly lower than in serum-free media. Similarly erythroleukemia cells were induced to differentiate by exposure to dimethylsulfoxide, in the presence of non-mouse serum. When mouse serum was added to the culture, erythroid cell differentiation is inhibited (Parker et al., 1981, Leuk. Res. 5: 123). In addition, hepatocytes were induced to differentiate in culture by, e.g., addition of non-physiologic amounts of glucocorticoid hormones, dimethylsulfoxide, or phenobartitol, but these treatments have been found to alter normal ethanol metabolism or normal amounts and types of microsomal enzymes involved in drug metabolism (Paine et al., 1982, Blochem. Pharmacol. 31: 1175).

Conte and Tasat (1986, J. Steroid Biochem. 24:749) postulated that inhibition of rat epithelial cell differentiation by fetal calf serum may be due to the presence of vitamin A. Lin et al. (1987, Mol. Cell. Biol. 7:4324) identified an inhibitor of glucagon sensitivity in cultured kidney cells as being a fetal bovine serum factor of 50–100 kD.

SUMMARY OF THE INVENTION

In general, the invention features a method of reducing the loss of differentiative functions of cells cultured in culture medium containing serum which includes an inhibitor of tissue specific function, the method comprising treating the serum or serum-containing medium to remove or inactivate the inhibitor; and serum or serum-containing medium treated so as to reduce the loss of differentiative functions of cultured cells.

In preferred embodiments, the method includes a treating step comprising contacting the serum or serum-containing medium with a chemical agent having a first domain having a negative charge and a second domain which is hydrophobic. Preferably, the treating step comprises removing the inhibitor from serum containing medium or serum by applying said serum or serum containing medium or a fraction thereof to a column on which is immobilized the chemical agent, the agent being capable. Preferably, the chemical agent is, Cibacron Blue.

The method may also include a treating step in which the chemical agent comprises a detergent, and the method comprises inactivating the inhibitor by (a) incubating the serum with the detergent, to form inhibitor-detergent complexes, (b) removing any excess unbound detergent from inhibitor-depleted serum. Preferably, the detergent comprises sodium dodecyl sulfate or N-lauroylsarcosine.

The invention may help solve a number of problems currently faced by cell culturing facilities. Individual lots of serum currently must be tested in cell culture before use to determine the amount of inhibition of cellular growth and/or differentiation; fetal calf serum is often preferred over calf serum because it does not inhibit tissue specific function as much. The use of serum in cell culture is a major cost factor, as serum is sometimes scarce and large amounts are required, particularly for continuous fermentation of, e.g., transformed cells. The method of the invention may eliminate the need for testing, as well as the use of the more expensive, less readily-available types of serum, e.g., neonatal or fetal calf serum. The invention could also eliminate some problems encountered in culturing transformed cells, e.g., genes that are cloned and expressed in cells that are cultured in medium containing serum often depend for expression upon the differentiated state of the cell. The use of inhibitor-depleted serum to culture transformed cells would enable cells in culture to maintain their differentiated state; consequently, the gene, whose expression depends upon the differentiated state of the cells, will produce higher levels of gene product.

Other features and advantages of the invention will be apparent from the following description of the preferred embodiments thereof, and from the claims.

PREFERRED EMBODIMENTS

The drawings will first be described.
Drawings

CHARACTERIZATION OF SERUM INHIBITORY FACTOR

Serum and plasma contain a factor or factors which cause a decrease in levels of mRNA for albumin, as well as a decrease in the transcriptional activities of other genes related to differentiative function. One particular serum inhibitory factor was characterized as follows. In fetal calf serum (FCS), the inhibitory factor was found to be relatively stable to heat, acid treatment, and charcoal and organic extractions; it was not dialyzable, even at pH 3, and was still active in delipidated serum. When serum was ammonium sulfate precipitated, the major inhibitory activity was found in the 70% pellet. The apparent molecular weight of the inhibitory factor was determined to be about 67 kD (in the range 50 to 100 kD), with a probable molecular weight of about 70 kD. The inhibitory activity bound DEAE-Sephacel and Cibacron Blue-agarose, but failed to bind heparin or conconavalin A. Treatment of serum with SDS or N-lauroylsarcosine at 37° C., followed by dialysis, eliminated the serum inhibitory activity.

In the experiments which yielded these observations, inhibition was determined by measuring specific mRNA levels in hepatocytes cultured in treated serum-containing medium and then expressing this level as a percentage of the level of mRNA from cells cultured in control untreated serum-containing medium. mRNA levels were quantitated by Northern blot analysis using radioactive cDNA probes encoding either a portion of albumin or $\beta$-actin, and then subjecting the resultant autoradiograms to scanning densitometry. In more detail, the characterization experiments were carried out as follows.

Effect of Fetal Calf Serum on Hepatocyte mRNA Concentrations

The presence of FCS in culture medium was found to cause inhibition of cell differentiation or to cause dedifferentiation for many types of cells. For example, when primary cultures of rat hepatocytes were maintained in serum-free medium containing hormones or in medium containing 10% fetal calf serum, there was a loss of differentiative functions, as defined by albumin messenger RNA levels, in the serum-containing medium. Albumin mRNA levels were measured by extracting total RNA and performing Northern blot analysis (Maniatis et al., 1982, Molecular Cloning: A Laboratory Manual, Cold Springs Harbor, N.Y.) using albumin cDNA as a probe. Primary rat hepatocytes were maintained in culture in one of three types of media: HDM, (hormonally-defined medium contains insulin 10 ug/ml, glucagon 10 ug/ml, epidermal growth factor 50 ng/ml, human growth hormone 10 uU/ml, prolactin 2 mU/ml, linoleic acid 5 ug/ml, BSA 10 ug/ml, copper ($10^{-7}$M), selenium ($3 \times 10^{-10}$M), and zinc ($5 \times 10^{-11}$M) Enat et al. (1984) Proc. Natl. Acad. Sci. 81:1411-1415); SSM (10% fetal calf serum supplemented medium); or HDM & SSM (medium containing both hormones and serum). After 72 hours, total RNA was extracted from the cells according to the procedure of Feramisco et al. (1982) J. Biol. Chem. 257:11024-11031. RNA was also extracted from fresh rat liver cells (RAT) to compare the levels of specific mRNAs in cells taken directly from the liver rs. cultured liver cells.

Figure 1:
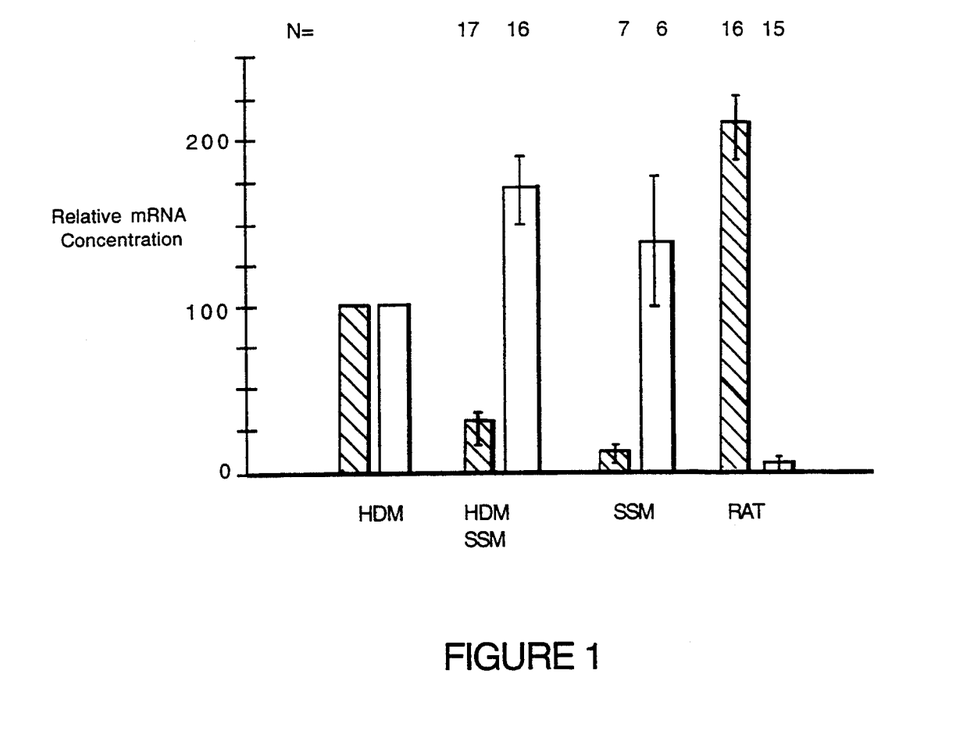
FIG. 1 is a graph which shows the relative albumin and $\beta$-actin mRNA concentrations in hepatocytes cultured in media containing fetal calf serum.

The RNA was subjected to Northern Blot analysis (Maniatis et al., supra) and identical samples of RNA were probed with one of two different cDNA probes, DNA encoding albumin (Zern et al., 1983, Hepatology 3:317) to detect albumin mRNA, or DNA encoding $\beta$-actin (Cleveland et al., 1980, Cell 20:95) to detect $\beta$-actin mRNA. FIG. 1 shows the results of this experiment. An autoradiogram of the Northern blot was scanned using a densitometer, and band intensities were expressed as a percentage of the level of albumin mRNA (solid bars) or $\beta$-actin mRNA (open bars) present in cells cultured in HDM. N=the number of comparisons to the HDM control in separate preparations of cultured hepatocytes. The results are expressed relative to the levels of albumin and $\beta$-actin mRNA from cells cultured in hormonally-defined medium, which are presented as 100%. FIG. 1 shows that the level of albumin mRNA in cells cultured in either medium containing serum (HDM & SSM or SM) decreases dramatically (30.4±3.55 percent or 10.2 ±3.12 percent, respectively), indicating a loss of liver specific albumin mRNA, by contrast, the level of $\beta$-actin mRNA increases in the presence of serum in both HDM & SSM and SSM (170±22 percent or 137±40 percent of the $\beta$-actin mRNA level in HDM, respectively).

The level of albumin mRNA is normally found to be higher in differentiated liver cells than in undifferentiated cells. The increase in $\beta$-actin mRNA levels in The serum-containing media demonstrates the decrease in the level of albumin mRNA is not due to a decrease in overall mRNA synthesis. Albumin mRNA concentration in fresh rat liver was 209+21 percent of the $\beta$-actin mRNA level in HDM.

Comparison of Plasma and Serum.

Plasma contains products of blood clotting, such as platelet derived growth factor (PDGF) and $\beta$-transforming growth factor ($\beta$-TGF). The results presented in Table I show that both plasma and plasma-derived serum, which does not contain factors released by platelet aggregation, exhibited inhibitory activity. Both plasma and plasma-derived serum were prepared by addition of 30 mM $CaCl_1$ followed by incubation at 20° C. for 1 hour. Both were then centrifuged to remove the clot and extensively dialyzed against PBS. Table I shows relative mRNA concentrations from Northern Blot analysis of mRNA obtained from hepatocytes cultured in media containing serum or plasma from different sources, and expressed as a percentage of the mRNA level found in hepatocytes cultured in HDM alone (100%). The results show that both serum and plasma from (experiment 1) a single fetal calf and (experiment 2) from unrelated pools of adult bovine serum and plasma contain the inhibitory activity. Inhibition is apparent in the decrease in albumin mRNA levels that is detected in hepatocytes cultured in medium containing 10% serum or 10% plasma-derived serum. Thus, the dominant inhibitory factor is not a platelet-derived factor, such as PDGR or $\beta$-TGF. The inhibitory activity in the adult bovine serum tested appeared less potent than fetal calf serum, although this serum had almost twice the protein concentration of fetal calf serum. Experiment 2 showed that albumin mRNA levels were 66% of the control level and $\beta$-actin mRNA levels were 71% in the presence of adult bovine serum; whereas, in experiment 1, these levels were 40-46% and 27-32%, respectively, in the presence of fetal calf serum. One lot of neonatal calf serum also exhibited considerable activity (experiment 3).

Heat Treatment of Serum.

The inhibitory activity was found to be quite stable to heat treatment (heating for 30 minutes at 60° C. or 80° C.). (Heat treatment at 56° C. for 30 minutes is the protocol usually used to produce "heat-inactiviated serum" with loss of complement activity.) Table II compares relative mRNA concentrations from hepatocytes cultured in medium containing heat treated serum. Fetal calf serum was heated at 60° C. or 80° C. for 30 minutes, and used as a 10% solution of medium in which hepatocytes were cultured for 72 hours. RNA was extracted from the cells and albumin-specific or β-actin-specific mRNA was analyzed on a Northern Blot. Experimental mRNA levels were expressed relative to the control mRNA levels from cells cultured in hormonally defined medium (HDM). In four experiments (identical except for experiment 3, in which the fetal calf serum was frozen at −20° C. and did not go into solution well), the presence of fetal calf serum in the medium was found to result in a 2.5-12 fold decrease in albumin mRNA levels, and that heat treated serum caused less of a decrease (1.5-2.5 fold) than untreated serum. Thus, the inhibitory activity was found to be weakened, but not abolished, by heat treatment of the serum.

Organic Extracts of Serum.

Organic extracts of fetal calf serum were prepared to determine if the inhibitory factor is a lipid or requires a lipid for its action. Lipids were extracted from serum with either 5 volumes of chloroform:methanol (2:1) or 5 volumes chloroform:methanol:water (1:1:0.3) (the latter mixture extracts more polar lipids); the aqueous phases were then discarded; and the organic phases were dried under nitrogen. As a control for possible interfering substances in the chloroform:methanol, phosphate buffered saline (PBS) was extracted with chloroform:methanol (2:1) and the organic phase dried under nitrogen. The organic extracts were resuspended in RMPI 1640 containing 1 mg/ml BSA.

In experiment 2, 10 ml of fetal calf serum had acetic acid added to 1M. This was accomplished as follows. A Sep-Pak (ODS-silica) cartridge was washed with 5 ml methanol and then 5 ml distilled water. The serum was passed through the cartridge and the cartridge was washed again with 5 ml distilled water. The adsorbed material then was eluted with 5 ml of methanol and the methanol was brought to dryness under nitrogen and kept at −20° C. until use. Before use, the extract was dissolved in 10 ml of PBS with 40 mg/ml of dialyzed bovine serum albumin (BSA). The same albumin preparation was used as the BSA control in experiment 2.

in experiment 3, fetal calf serum was delipidated by a previously reported procedure (Rothblat etal. (1976) In Vitro, 12:554-557). Twenty ml of fetal calf serum was added to 200 ml of iced ethanol:acetone (1:1) and stirred on ice for 2 hours, then the precipitated protein was collected on a Buchner funnel and dried with a small volume of ether. The dried material was scraped from the filter paper, stored dry at −20° C., and then redissolved in 20 ml PBS.

As in the preceding experiments, hepatocytes were cultured in medium containing control serum or organic extracts of treated serum, and RNA was extracted and subjected to Northern Blot analysis to measure albumin and β-actin mRNA levels. The results presented in Table III show a slight decrease in the albumin mRNA level in the chloroform:methanol or chloroform: methanol:water extracted serum compared with the chloroform:methanol extracted PBS (experiment 1, 68%, 70%, and 83%, respectively). Extraction of acidified serum with an ODS-silica cartridge (Sep-Pak) failed to remove significant inhibitory activity (experiment 2, 95% compared to the control level of 115%). In addition, serum protein delipidated by extraction and precipitation in ethanol:acetone (1:1) retained significant inhibitory activity (experiment 3, 38% compared to 28% level of untreated FCS. The ethanol: acetone delipidation method removes over 98 percent of the major lipid classes (Rothblat, et. al. (1976) In Vitro, 12:554). This experiment demonstrated that the inhibitory activity is not a lipid, and does not depend on a lipid for its action.

Charcoal Extraction of Serum.

To test the possibility that the inhibitory factor is a small molecule, perhaps bound to a serum protein, serum was treated with activated charcoal, using a protocol developed for the removal of tightly bound fatty acids from albumin using activated charcoal at pH 3 (Shen, R. F. (1967) J. Biol. Chem., 242:173). Briefly, serum was kept on ice and titrated to pH 3 with HCl; 20 mg of activated charcoal were added per ml of serum and the serum was stirred for two hours before it was neutralized. The neutralized serum was then extensively dialyzed against PBS at 4° C. "Acid-treated" serum or "charcoal-treated" serum were treated only with acid or charcoal, respectively.

Table IV shows that the level of albumin mRNA, determined by Northern blot analysis from hepatocytes cultured in medium containing either uncreated fetal calf serum or any of the three treated serums (acid, charcoal, or acid/charcoal), decreased to about the same degree, ranging from 28% for untreated FCS to 21-37% for treated FCS. A control experiment was done in which bovine serum albumin (BSA) was treated with charcoal. Addition of BSA or charcoal-treated BSA to 40 mg/ml in the culture medium slightly increased the levels of albumin mRNA. Thus, even the treated serum retained most of its inhibitory activity, rendering it unlikely that the dominant inhibitory activity is a small organic ligand.

Dialysis of Serum.

In order to determine if dialysis of serum could remove the inhibitory activity, hepatocytes were cultured in medium containing dialyzed serum and RNA was extracted and albumin-specific mRNA quantitated, as described above. Fetal calf serum was dialyzed against PBS using a spectra/Por 6 dialysis membrane with a 1000 mw cutoff or a spectra/Por 2 membrane with a 10,000-12,000 mw cutoff. In experiment 2, serum was dialyzed against calcium-free PBS with 10 mM EDTA, then against PBS to remove the EDTA. Serum was also dialyzed against 1M acetic acid, then dialyzed against PBS to remove the acetic acid, or treated with 10 mM dithiothreitol, pH 6.5 at 4° C. for 24 hours, then dialyzed extensively against PBS. The control serum contained BSA (40 mg/ml) which was also dialyzed against the buffers listed in experiment 2.

Table V compares relative mRNA concentrations from hepatocytes cultured in media containing dialyzed serum, and shows that dialysis of serum has no appreciable effect on the decrease of albumin mRNA synthesis and therefore also has little effect on the inhibitory activity (experiment 1). Dialysis of serum against calcium-free PBS with 10 mM EDTA failed to diminish the inhibitory activity significantly (experiment 2). Dialysis of serum against 1M acetic acid, which releases bound ligands from albumin, did not diminish the activity significantly. Serum was treated with dithiothreitol to release ligands bound in mixed disulfide linkage to the single free sulfhydryl of BSA. Such a covalently bound ligand should be rendered dialyzable by this treatment, but most of the inhibitory activity remained (experiment 2).

Ammonium Sulfate Precipitation of Serum.

Figure 2:
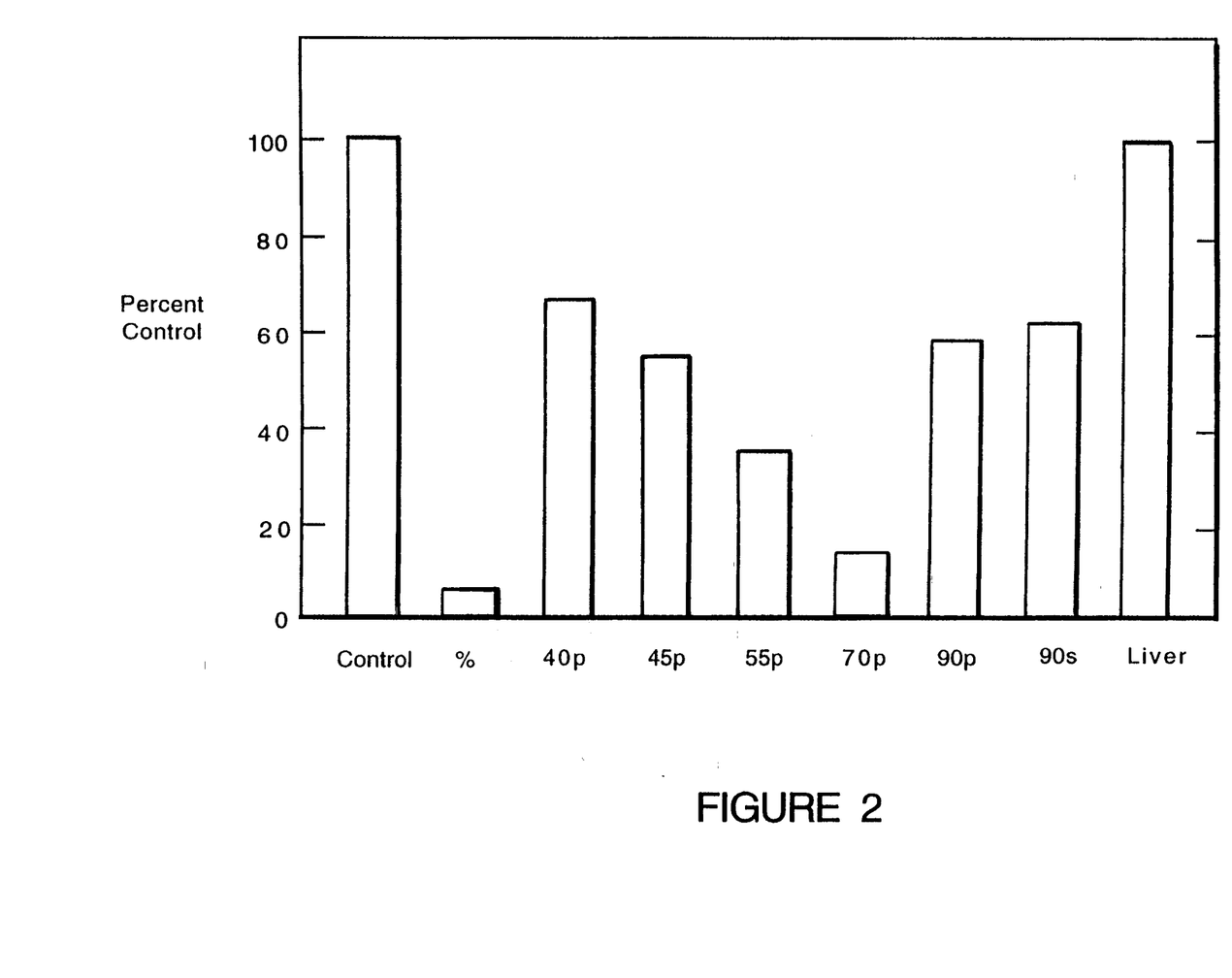
FIG. 2 is a graph which shows relative mRNA concentrations in hepatocytes cultured in media containing various ammonium sulfate fractions.

The inhibitory factor was partially purified by subjecting the serum to sequential ammonium sulfate precipitations, to the saturations indicated in FIG. 2. The resulting pellets were dialyzed against RPMI 1640 for use in cell culture. Primary rat hepatocytes were maintained in HDM for 72 hours with the additions indicated in FIG. 2: S = 10% fetal calf serum; 40 P, 45 P, 55 P, 70 P, 90 P = 40%, 45%, 55%, 70%, and 90% ammonium sulfate pellet, respectively; and 90 S = dialyzed supernatant of the 90% pellet. Columns indicate albumin mRNA levels relative to the HDM control of 100%. Most of the activity was found in the 45 or 50 percent supernatant, or the 70 percent pellet, which typically contains about a third of serum protein, including $\beta$-transforming growth factor.

Proteolytic Digestion of the Inhibitory Factor.

The 70% ammonium sulfate pellet was digested with the proteolytic enzyme trypsin to determine if the inhibitory factor was a protein or a peptide. Fetal calf serum was ammonium sulfate precipitated and the 50% supernatant-70% pellet was dialyzed against PBS. The ammonium sulfate precipitate (ASP) from 10 ml of serum was added to 10 mg trypsin and incubated at 37° C. for 2 hours. Another aliquot of the ASP was incubated under the same conditions, but without trypsin. 10 mg of soybean trypsin inhibitor (STI) was then added to the trypsin-digested sample and a control. The samples were dialyzed against PBS, using a Spectra/Por 3 3500 mw cut off membrane. The protein concentration of each serum fraction was: FCS, 44.2 mg/ml; 70% ASP, 19.7 mg/ml; ASP & trypsin & STI, 15.4 mg/ml; ASP & STI, 18.0 mg/ml. SDS-PAGE showed substantial proteolysis. Measurable protein remaining after dialysis (3,500 molecular weight 5 cutoff) was 15.4 mg/ml in the trypsinized sample, compared to 18.0 mg/ml for the control with soybean trypsin inhibitor but no trypsin.

Table VI compares mRNA levels in hepatocytes cultured in media containing proteolytic digests of the 70% ASP of serum, and shows that tryptic digestion of the 70% pellet eliminated the inhibitory activity. However, it is possible that tryptic digestion generates peptides that merely increased levels of albumin mRNA or antagonized the inhibitory factor. This ammonium sulfate pellet contains the major amount of $\alpha$-1 antiprotease activity of serum and, therefore, excess proteolytic enzyme was added. There was a lower survival rate for hepatocytes cultured in the presence of proteolytic digests of the 70% pellet. This may have resulted from inhibition of growth by the peptides generated, or from protease activity that persisted despite the addition of soybean trypsin inhibitor.

Molecular weight of the Inhibitory Factor.

Figure 3:
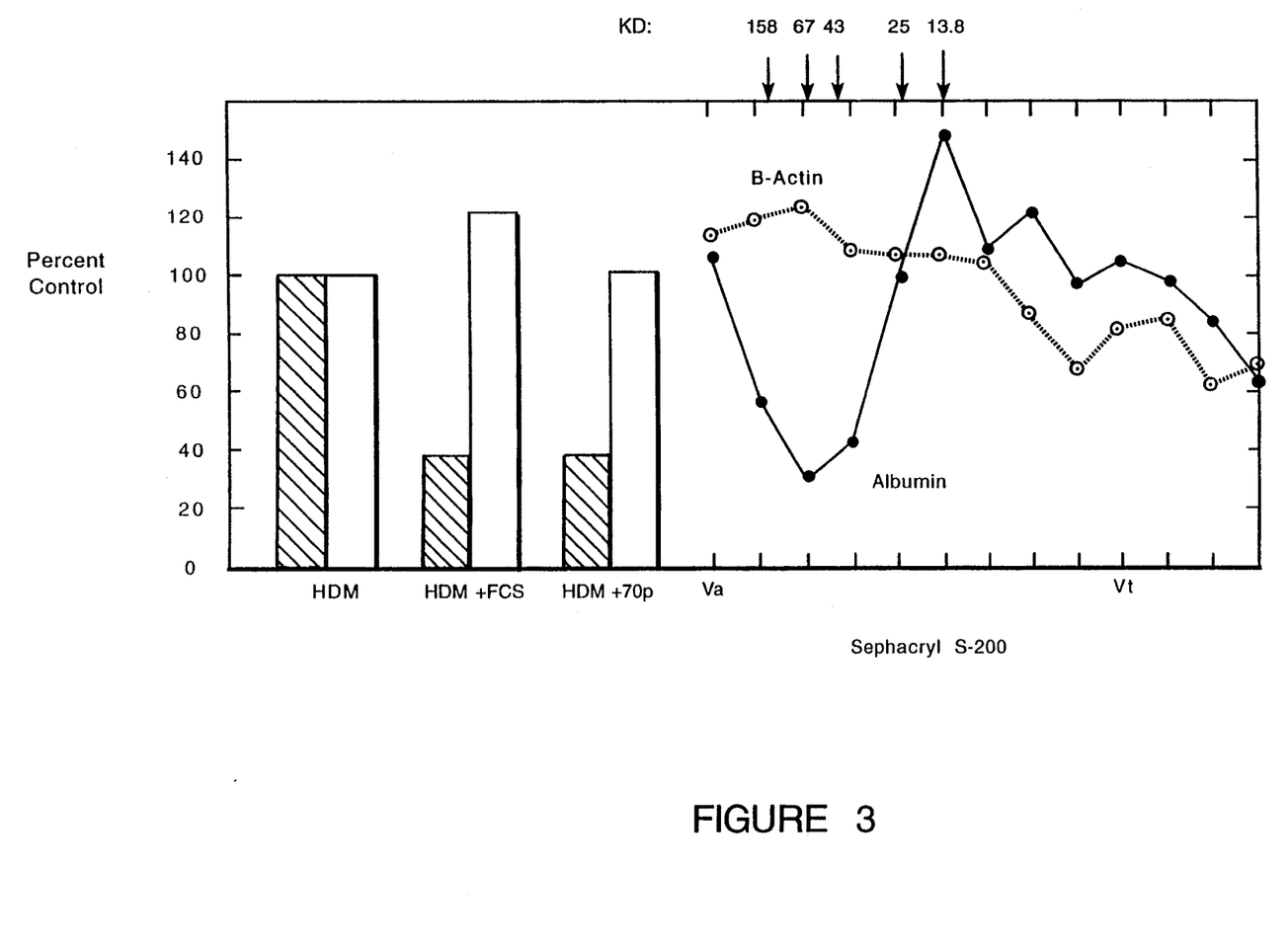
FIG. 3 is a graph which shows relative mRNA concentrations in cells cultured in media containing fetal calf serum that has been subject to molecular sieve chromatography of the 50–70% ammonium sulfate pellet.

In order to determine the molecular weight of the inhibitory factor, the 70% pellet was subjected to molecular sieve chromatography on Sephacryl S-200. A 20 ml sample of 50–70% ammonium sulfate pellet representing 53 mi of serum was applied to a Sephacryl S-200 column 1.6×92.5 cm, bed volume 185 ml) equilibrated with RPMI 1640. Fractions were collected into pools of 13.6 ml, starting just before the void volume. Ten fractions just bracket the void volume and total bed volume. For each plate of hepatocytes with 10 ml of medium, 2 ml of the column fraction was used. Cells were grown in the presence of HDM and the various fractions for 3 days, then the total RNA was extracted and probed for albumin and $\beta$-actin mRNA. FIG. 3 shows these results. The scales show the mRNA levels in arbitrary densitometric units; 70 P = 50–70% ammonium sulfate pellet equivalent to 10% FCS; closed circles or bars represent albumin mRNA; open circles or bars represent $\beta$-actin mRNA.

The peak inhibitory activity was found at a molecular weight of approximately 67 kD. However, since resolution was limited by the 20 ml volume applied to the column, the molecular weight was determined to be between 50 and 100 kD. A small ligand might have an apparent molecular weight in this range if it binds tightly to serum albumin or another protein. This possibility was investigated by subjecting the 70% pellet to molecular sieve chromatography on Biogel P-60 (2.5×58 cm column, bed volume 290 ml equilibrated in 1M acetic acid). 13 ml of 70% ammonium sulfate pellet, representing 26 ml of fetal calf serum, was equilibrated to 1M in acetic acid and applied to the column. Fractions of 5 ml were taken, pooled, and placed in dialysis bags; the volume was then reduced with sodium carboxymethylcellulose (Aquacide II), and the fractions were extensively dialyzed against PBS. Fractions were used for hepatocyte cell culture in twice the concentrations they represent in serum. After chromatography of the serum, the column was calibrated with ovalbumin (43 kD), RNAse A (13.8 kD), and insulin (6 kD) in 1M acetic acid. At pH 2.7, albumin and other serum proteins should be unable to bind small ligands.

Figure 4:
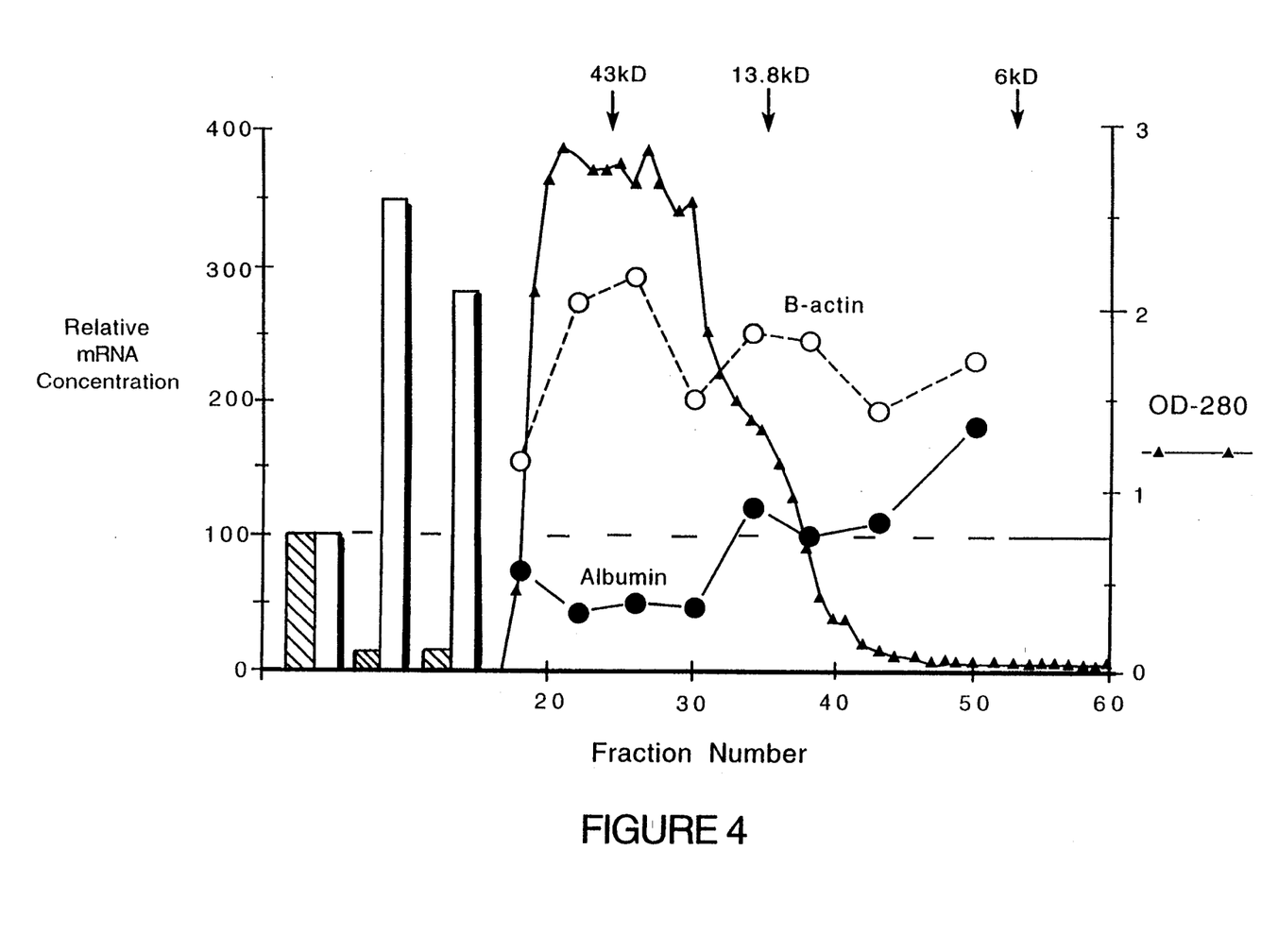
FIG. 4 is a graph which shows relative mRNA concentrations in hepatocytes cultured in media containing serum that has been fractionated on a Biogel P-60 column in 1M acetic acid.

FIG. 4 shows that the inhibitory activity corresponded to a broad initial peak of protein, while the trailing shoulder had no activity. The mid-point of inhibitory activity corresponded approximately to the mobility of ovalbumin (43 kD). These results were consistent with another experiment in which the inhibitory activity eluted from the same column in a pool consisting of fractions 20 through 40. Later pools, extending through fraction 120, had no activity (data not shown).

Purification of the Inhibitory Activity by DEAE-Sephacel Chromatography.

Figure 5:
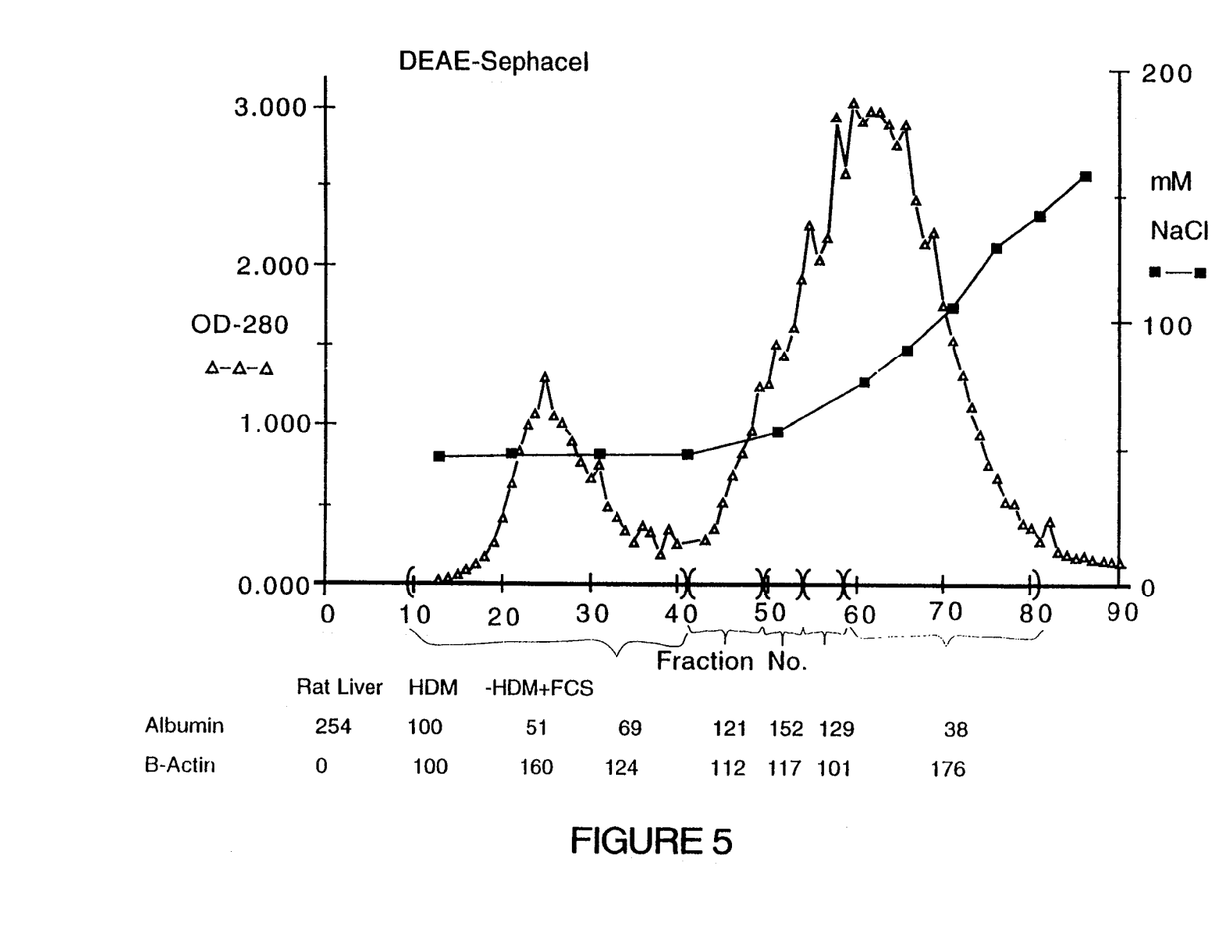
FIG. 5 is a graph which shows relative mRNA levels in hepatocytes cultured in media containing fractions from DEAE-Sephacel chromatography of the 50–70% ammonium sulfate pellet.

The 50–70% pellet from 50 ml of fetal calf serum was extensively dialyzed against 25 mM sodium phosphate (pH 7.6)–50 mM NaCl and applied to a column of DEAE-Sephacel (2.6×22 cm, 118 ml) equilibrated with the same buffer, as shown in FIG. 5. After an initial wash, a gradient from 50 to 250 mM NaCl was applied, and 5.6 ml fractions were collected. NaCl concentration is shown, as measured by conductance. Protein was put into five pools as indicated by the brackets on the x-axis. The pools were put into dialysis bags, the volume reduced with Aquacide II, and the bags were dialyzed against PBS, for use in cell culture. Pools were used for hepatocyte culture three times concentrated over the original serum. Hepatocytes were cultured for 72 hours in HDM and the indicated serum fractions, then hepatocyte RNA was extracted for Northern blot hybridization. mRNA levels are indicated below the graph, expressed as percent of the HDM control. Most of the activity adhered to the column and eluted in the pool of protein that eluted after the peak $OD_{280}$. This pool contained about 41% of the total $OD_{280}$ units, and was enriched in albumin.

Cibacron Blue-Agarose Chromatography.

Cibacron Blue, when coupled to agarose, is a dye having two domains, the first of which has a strong negative charge and therefore binds positively charged molecules, and the second of which is hydrophobic. Cibacron Blue-agarose chromatography was used in an effort to separate the inhibitory factor from serum albumin, with which it shares some properties. In both experiments 1 and 2, the ammonium sulfate precipitate in PBS was applied to a 100 ml bed volume of Cibacron-Blue agarose in Dulbecco's phosphate buffered saline. Serum fractions were collected, pooled, concentrated, and dialyzed against PBS, before they were added to the culture medium. In the first experiment, the PBS did not include $CaCl_2$; in the second, $CaCl_2$ was added. (General methods for the use of Cibacron Blue F3-GA agarose to fractionate serum proteins have been described previously (Gianazza, E. and Arnaud, P. (1982) Biochem. J. 201:129 and 203:637)).

In experiment 1, the 70% ASP of 30 ml of FCS (i.e., 429 mg protein) was applied to the Cibacron Blue-agarose column. The protein content of the fraction collected from the column were: PBS, 156.3 mg; PBS "wash," 18.9 mg; and PBS with 1M NaCl, 144.3 mg. The protein content of all of these fractions together accounts for 319.5 mg of the 429 mg applied to the column. In experiment 2, the 70% ASP of 30 ml of FCS (i.e., 571 mg protein) was applied to the Cibacron Blue-agarose column. The column was then equilibrated with Dulbecco's phosphate buffered saline (D-PBS), including calcium, and eluted sequentially with D-PBS, D-PBS with 1M NaCl, D-PBS with 2M NaCl, and with 0.5M NaSCN. The protein content of the fractions were: PBS, 189 mg; PBS with 1M NaCl, 195 mg; PBS with 2M NaCl, 14,85; and 0.5M NaSCN wash, 24.9 mg, which accounts for a total protein recovery of 423.7 mg of the 591 mg of protein applied to the column.

Hepatocytes were cultured in media containing the above-described serum fractions, and RNA was extracted and subjected to Northern blot analysis using albumin or β-actin DNA probes. The results, shown in Table VII, demonstrated that no inhibitory activity was eluted with up to 1M NaCl, although some albumin was eluted (experiment 1). In experiment 2, in which the 70% pellet was applied to Cibacron Blue-agarose in PBS with calcium, some activity was eluted with 1M NaCl, and no further activity was eluted with higher NaCl or with sodium thiocyanate. These results indicate that the inhibitory factor binds to Cibacron Blue-agarose.

Other Chromatography Media.

The inhibitory serum factor did not bind three other commonly used chromatographic media. The 70% ammonium sulfate pellet was applied after dialysis against an appropriate buffer. Heparin-agarose did not bind the serum factor, after either a continuous application of serum to a heparin-agarose column at 4° C. or batch processing at 20° C., although heparin antagonizes the serum inhibitory activity in hepatocyte culture. Dowex 50w cation exchange resin in 0.1M Tris-acetate at pH 3.0 and at 4° C. failed to bind the inhibitory activity. Conconavalin A sepharose, although it binds many serum glycoproteins, did not bind the inhibitory factor. Detergent Treatment of Serum.

Incubation of some detergents with serum, or with the active ammonium sulfate fraction of serum, caused loss of the inhibitory activity. Fetal calf serum is incubated with a detergent, either sodium dodecyl sulfate (SDS) or N-lauroyl sarcosine, at a concentration of 1 milligram per milliliter (0.1 percent) at 37° C. for two hours. The serum was extensively dialyzed against four changes of phosphate buffered saline at 40° C. to remove all unbound detergent. For this purpose, a dialysis membrane with a molecular weight cutoff of 3,500 can be used, or a more porous membrane may be used to remove detergent. Following dialysis, the serum was filter sterilized for use in cell culture, typically as 10 percent fetal calf serum. Hepatocytes were cultured in dialyzed detergent-treated serum-containing medium for 72 hours before RNA was extracted. Table VIII shows that neither the presence of the 0.1% SDS-treated 10% APS fraction, nor the presence of unfractionated serum that has been treated with 0.1% SDS, resulted in a decrease in albumin mRNA levels (experiment 1). This experiment demonstrated that treatment of serum with SDS at a concentration of 0.1% can inactivate the inhibitory factor. The effect of SDS appears to be concentration dependent; dilution of SDS to 0.01% or 0.001% resulted in greater inhibition of albumin mRNA levels. In addition, a low concentration of SDS (0.001%), added to the serum without subsequent dialysis had little effect on the inhibitor. Several detergents which are weaker anions than SDS, e.g., sodium dodecyl sulfonate and sodium octyl sulfonate, were less effective than SDS in preventing inhibition; oleyl glycerol and CHAPS had little effect. N-lauroyl sarcosine (N-methyl-N-lauroyl glycine) was at least as effective as SDS. The two sulfonate detergents are more dialyzable than SDS.

OTHER EMBODIMENTS

Other embodiments are within the following claims. The chemical agent that is used to deplete serum of its differentiation inhibiting or dedifferentiating activity may be, a detergent, or any other agent. All that is required of the chemical agent is that it have two domains, one of which is an anionic hydrophilic portion such as carboxylate, sulfate, or sulfonate, and a hydrophobic portion, such as a fatty acid, fatty alcohol, or naphthenic acid. Any serum may be used that is capable of promoting cellular longevity in culture, e.g., fetal calf serum, adult bovine serum, goat serum, or horse serum.

TABLE I

| COMPARISON OF PLASMA AND SERUM (Relative mRNA concentrations expressed as percent of HDM) | | | | | | |
|---|---|---|---|---|---|---|
| | Exp. 1 | | Exp. 2 | | Exp. 3 | |
| | Albumin | B-actin | Albumin | B-actin | Albumin | B-actin |
| Rat Liver | — | — | 343 | 0 | 155 | 0 |
| HDM | 100 | 100 | 100 | 100 | 100 | 100 |
| HDM + FCS | 37 | 67 | 45 | 126 | 33 | 156 |
| HDM + Single-donor fetal calf serum | 40 | 27 | — | — | — | — |
| HDM + Single-donor fetal calf plasma | 46 | 32 | — | — | — | — |
| HDM + Adult bovine serum (pooled) | — | — | 66 | 71 | — | — |
| HDM + Adult bovine | — | — | 4.0 | 82 | — | — |

TABLE I-continued
COMPARISON OF PLASMA AND SERUM
(Relative mRNA concentrations expressed as percent of HDM)

|  | Exp. 1 | | Exp. 2 | | Exp. 3 | |
| --- | --- | --- | --- | --- | --- | --- |
|  | Albumin | B-actin | Albumin | B-actin | Albumin | B-actin |
| plasma (pooled) HDM + Neonatal calf serum (pooled) | — | — | — | — | 22 | 117 |

TABLE II
EFFECT OF HEAT-TREATED SERUM
(Relative mRNA concentrations expressed as percent of HDM)

|  | Exp. 1 | | Exp. 2 | | Exp. 3 | | Exp. 4 | |
| --- | --- | --- | --- | --- | --- | --- | --- | --- |
|  | Albumin | B-actin | Albumin | B-actin | Albumin | B-actin | Albumin | B-actin |
| Rat Liver | 180 | 0 | 163 | 0 | 182 | 0 | 340 | 0 |
| HDM | 100 | 100 | 100 | 100 | 100 | 100 | 100 | 100 |
| HDM + FCS | 7.7 | 108 | 26 | 108 | 42 | 192 | 45 | 126 |
| HDM + FCS (60°) | — | — | 26 | 82 | — | — | 65 | 116 |
| HDM + FCS (80°) | 40 | 106 | 42 | 51 | 103 | 176 | 60 | 126 |

TABLE III
ORGANIC EXTRACTS OF FETAL CALF SERUM
(Relative mRNA concentrations expressed as percent of HDM)

|  | Exp. 1 | | Exp. 2 | | Exp. 3 | |
| --- | --- | --- | --- | --- | --- | --- |
|  | Albumin | B-actin | Albumin | B-actin | Albumin | B-actin |
| Rat Liver | 180 | 0 | 197 | 0 | — | — |
| HDM | 100 | 100 | 100 | 100 | 100 | 100 |
| HDM + FCS | 7.8 | 108 | 37 | 378 | 28 | 220 |
| HDM + Chloroform:Methanol Control | 83 | 107 | — | — | — | — |
| HDM + C/M (2:1) extract of FCS | 68 | 94 | — | — | — | — |
| HDM + C/M/water (1:1:0.3) extract of FCS | 70 | 112 | — | — | — | — |
| HDM + BSA control | — | — | 115 | 363 | — | — |
| HDM + Sep-Pak extract of FCS + BSA | — | — | 95 | 383 | — | — |
| HDM + Delipidated Serum | — | — | — | — | 38 | 175 |

TABLE IV
EFFECT OF CHARCOAL-TREATED SERUM
(Relative mRNA concentrations expressed as percent of HDM)

|  | Albumin | B-Actin |
| --- | --- | --- |
| HDM | 100 | 100 |
| HDM + FCS | 28 | 220 |
| HDM + Acid-treated FCS | 21 | 203 |
| HDM + Acid/charcoal-treated FCS | 37 | 124 |
| HDM + Charcoal-treated FCS | 36 | 196 |
| HDM + BSA | 121 | 284 |
| RDM + Charcoal-treated BSA | 125 | 273 |

TABLE V
DIALYSIS OF SERUM
(Relative mRNA concentrations expressed as percent of HDM)

|  | Exp. 1 | | Exp. 2 | |
| --- | --- | --- | --- | --- |
|  | Albumin | B-actin | Albumin | B-actin |
| Rat Liver | 180 | 0 | 393 | 1 |
| HDM | 100 | 100 | 100 | 100 |
| HDM + FCS | 22 | 108 | — | — |
| HDM + Dialyzed FCS (1 kD MWCO) | 33 | 148 | 30 | 167 |
| HDM + Dialyzed FCS (14 kD MWCO) | 31 | 166 | — | — |
| HDM + FCS Dialyzed vs. EDTA | — | — | 57 | 225 |
| MM + FCS Dialyzed vs. 1 M Acetic Acid | — | — | 51 | 174 |
| HDM + FCS Dialyzed after Dithiothreitol treatment | — | — | 57 | 234 |
| HDM + Dialyzed Bovine Serum Albumin | — | — | 183 | 164 |

TABLE VI
PROTEOLYTIC DIGESTION OF THE 70 PERCENT AMMONIUM SULFATE PELLET

|  | Albumin | B-actin |
| --- | --- | --- |
| Rat Liver | 318 | 0 |
| HDM | 100 | 100 |
| HDM + FCS | 37 | 378 |
| HDM + 70% Asp | 42 | 505 |
| HDM + Trypsin digest of | 164 | 217 |

TABLE VI-continued

PROTEOLYTIC DIGESTION OF THE 70 PERCENT AMMONIUM SULFATE PELLET

|  | Albumin | B-actin |
|---|---|---|
| 70% ASP + Soybean Trypsin Inhibitor |  |  |
| HDM + 70% Asp + Soybean Trypsin Inhibitor | 39 | 521 |

TABLE VII

FRACTIONATION OF THE 70% AMMONIUM SULFATE PELLET BY CIBACRON BLUE AGAROSE CHROMATOGRAPHY

|  | Exp. 1 | | Exp. 2 | |
|---|---|---|---|---|
|  | Albumin | B-actin | Albumin | B-actin |
| Rat Liver | 338 | 14 | 197 | 0 |
| HDM | 100 | 100 | 100 | 100 |
| HDM + FCS | 56 | 154 | 37 | 378 |
| HDM + ASP | — | — | 42 | 505 |
| Cibacron Blue-Agarose: |  |  |  |  |
| PBS | 136 | 188 | 70 | 419 |
| "wash" | 187 | 150 | — | — |
| 1 M NaCl | 118 | 191 | 48 | 436 |
| 1 M NaCl | — | — | 102 | 297 |
| 0.5 M NaSCN | — | — | 106 | 136 |

TABLE VIII

EFFECT OF DETERGENT TREATMENT OF SERUM
(Relative mRNA concentrations expressed as a percent of HDM)

|  | Exp. 1 | | Exp. 2 | |
|---|---|---|---|---|
|  | Albumin | B-actin | Albumin | B-actin |
| Rat Liver | 393 | 16 | 274 | 0 |
| HDM | 100 | 100 | 100 | 100 |
| HDM + FCS | 30 | 167 | 50 | 133 |
| HDM + 70% ASP | 39 | 97 | — | — |
| HDM + 70% ASP Treated with 0.1% SDS | 139 | 234 | — | — |
| HDM + FCS Treated with 0.1% SDS | — | — | 119 | 80 |
| HDM + FCS Treated with 0.01% SDS | — | — | 67 | 108 |
| HDM + FCS Treated with 0.001% SDS | — | — | 48 | 95 |
| HDM + FCS, with 0.001% SDS added (No dialysis) | — | — | 59 | 111 |
| HDM + FCS treated with 0.1% sodim decyl sulfonate | — | — | 78 | 106 |
| HDM + FCS treated With 0.1% sodium octyl sulfonate | — | — | 71 | 140 |
| HDM + FCS treated with 0.1% N-lauroyl sarcosine | — | — | 162 | 84 |
| HDM + FCS treated with 0.1% oleyl glycerol | — | — | 62 | 126 |
| HDM + FCS treated with 0.1% CHAPS | — | — | 52 | 133 |

We claim:

1. A method of treating serum or serum-containing medium for reducing the loss of differentiative functions of hepatocytes cultured in said serum or serum-containing medium, said method comprising:
   (a) contacting said serum or serum-containing medium with an anionic detergent in an amount sufficient to inactivate an inhibitor of hepatocyte differentiation in said serum or serum-containing medium, wherein said detergent contains a sulfate or a carboxylate ionic group;
   (b) incubating said serum or serum-containing medium which has been contacted with the anionic detergent in order to inactivate said inhibitor; and
   (c) removing unbound detergent from said serum or serum-containing medium.

2. The method of claim 1, wherein the amount of detergent used is 0.1% weight/volume.

3. The method of claim 1, wherein said detergent is sodium dodecyl sulfate or N-lauroylsarcosine.

4. The method of claim 2, wherein said detergent is sodium dodecyl sulfate or N-lauroylsarcosine.

5. The method of claim 1, wherein said serum is bovine serum.

6. The method of claim 2, wherein said serum is bovine serum.

7. The method of claim 3, wherein said serum is bovine serum.

* * * * *

UNITED STATES PATENT AND TRADEMARK OFFICE
CERTIFICATE OF CORRECTION

PATENT NO.  : 5,380,660

DATED       : January 10, 1995

INVENTOR(S) : Douglas M. Jefferson and David E. Johnston

It is certified that error appears in the above-identified patent and that said Letters Patent is hereby corrected as shown below:

Column 2, line 7, after "capable", add --of binding to the inhibitor--;

Column 2, line 31, delete "fetal";

Column 4, line 15, replace "SM" with --SSM--;

Column 10, line 12, replace "40°C." with --4°C.--;

Column 12, Table V, line 53, replace "MM" with --HDM--;

Column 13, Table VI, line 7, replace "521" with --527--;

Column 13, Table VII, line 25, replace "136" with --336--;

Column 13, Table VIII, line 41, "sodium" is misspelled.

Signed and Sealed this

Eighteenth Day of April, 1995

Attest:

BRUCE LEHMAN

Attesting Officer

Commissioner of Patents and Trademarks